United States Patent [19]

Sakuma et al.

[11] Patent Number: 4,608,127
[45] Date of Patent: Aug. 26, 1986

[54] DIBENZOFURAN DISTILLATION AND CRYSTALLIZATION PROCESS

[75] Inventors: Kiyoshi Sakuma, Tadao Tomioka, Sunao Tabuchi, Kihachiro Ohta, Masakazu Takeuchi, all of Kitakyushu, Japan

[73] Assignee: Nippon Steel Chemical Co. Ltd., Tokyo, Japan

[21] Appl. No.: 741,268

[22] Filed: May 28, 1985

Related U.S. Application Data

[63] Continuation of Ser. No. 406,224, Aug. 9, 1982, abandoned.

[30] Foreign Application Priority Data

Dec. 10, 1980 [WO] PCT Int'l Appl. ... PCT/JP80/00303

[51] Int. Cl.[4] .................. C07D 307/91; B01D 3/00; B01D 9/00
[52] U.S. Cl. ........................ 203/48; 203/71; 203/DIG. 11; 62/542; 549/460
[58] Field of Search ............... 549/460; 585/807, 804, 585/806, 815, 812; 260/707; 203/48, DIG. 11, 71; 23/295, 296; 62/542, 532

[56] References Cited

U.S. PATENT DOCUMENTS

| 2,931,841 | 4/1960 | De Vault | 585/815 |
| 2,953,504 | 9/1960 | Bole et al. | 203/48 |
| 3,031,463 | 4/1962 | Overholt et al. | 549/460 |
| 3,067,270 | 12/1962 | Weedman | 203/48 |
| 4,279,130 | 7/1981 | Finch et al. | 585/812 |

Primary Examiner—Wilbur Bascomb
Attorney, Agent, or Firm—John J. Byrne; Bradford E. Kile; Kevin M. O'Brien

[57] ABSTRACT

Separation and recovery of dibenzofuran of high purity is accomplished by distilling a coal tar fraction having boiling point range of 220° to 300° C. thereby producing a dibenzofuran fraction having a dibenzofuran content of not less than 30% by weight, a dibenzofuran-/acenaphthene molar ratio of not less than 1.3, and a fluorene/dibenzofuran molar ratio of not more than 0.05, then introducing the dibenzofuran fraction obtained as described above into a continuous crystallization purification unit provided with a cooling zone for crystallization of the feed, a heating zone for melting the purified crystals, and a refining zone for enabling crystals being transferred from said cooling zone to said heating zone to come into counter current contact with a mass of molten crystals midway along the path between said two zones, and subjecting the dibenzofuran fraction to continuous crystallization purification therein.

12 Claims, 4 Drawing Figures

DIBENZOFURAN DISTILLATION AND CRYSTALLIZATION PROCESS

This is a continuation of application Ser. No. 406,224, filed Aug. 9, 1982, now abandoned.

DESCRIPTION

1. Technical Field

This invention relates to a process for producing dibenzofuran. More particularly, this invention relates to a process for producing dibenzofuran by subjecting a dibenzofuran fraction, which is obtained from a specific distillation of dibenzofuran containing coal tar fractions, to a continuous crystallization purification.

2. Background of Art

Dibenzofuran is a white crystalline solid substance having a boiling point of 288° C. and a melting point of 83° C. It is one of the compounds contained relatively in quantity in coal tar. Some of the dibenzofuran derivatives are useful as raw materials for dyestuffs, anticeptics, insecticides, etc. Dibenzofuran itself is also useful as a raw material for the production of o-phenylphenol.

Generally coal tar is separated by distillation into pitch and tar oils such as light oil, carbolic oil, naphthalene oil, wash oil and anthracene oil. Further from these fractions, useful products are obtained as required through such treatments as distillation, crystallization and extraction. Dibenzofuran is contained in the fractions ranging from naphthalene oil to pitch. The dibenzofuran content is about 15 to 30% by weight in wash oil and about 5 to 10% by weight in anthracene oil. Efforts have been made to recover dibenzofuran from these fractions.

U.S. Pat. No. 2,953,504 discloses a method for separating acenaphthene, dibenzofuran and fluorene from aromatic oils, for example, coal tar fractions having boiling point range of 260° to 300° C. This method comprises distilling the aromatic oils to get a fraction boiling at about 265° to 279° C., a fraction boiling at about 279° to 288° C., and a fraction boiling at about 288° to 299° C. separately, then cooling the fractions thereby causing crystallization therein, subsequently centrifuging the cooled fractions thereby completely separating them into a mother liquor and crystals, and collecting the crystals as product.

Since acenaphthene, fluorene, methyl naphthalene and many others components which have close boiling points with dibenzofuran are contained in large amounts in the coal tar fractions, it is extremely difficult to produce dibenzofuran of high purity only by distillation from such coal tar fractions. The idea of adopting the steps of crystallization and centrifugation subsequent to the step of concentration which is effected to a certain extent, therefore, may be justly called an advantageous approach. The inventors' research, however, has ascertained that no dibenzofuran of high purity is obtained by a method which comprises rectifying a coal tar fraction such as, wash oil thereby producing a fraction having an increased dibenzofuran content and subjecting this new fraction to an ordinary crystallization process, i.e. cooling while stirring the fraction of the increased dibenzofuran content thereby causing crystallization therein and producing a slurry containing crystals, and centrifuging this slurry thereby separating crystals and a mother liquor In the manufacture of a high purity product by the crystallization, formation of a eutectic mixture and formation of a solid solution constitute the factors that impede enhancement of the purity. Further in the case of an operation of centrifugation residual mother liquor poses a problem. In the dibenzofuran fraction which is obtained by distillation and concentration of the coal tar fraction, a number of components coexist as impurities in a large amount. Numerosity of the factors impedimental to the enhancement of purity, is easy to appreciate.

An object of this invention, therefore, is to provide a novel process for producing dibenzofuran. Another object of this invention is to provide a process for producing dibenzofuran of high purity.

DISCLOSURE OF INVENTION

These objects of the invention are accomplished by a process for producing dibenzofuran, which comprises distilling a coal tar fraction containing dibenzofuran thereby producing a dibenzofuran fraction having a dibenzofuran content of not less than 30% by weight, a dibenzofuran/acenaphthene molar ratio of not less than 1.3, and a fluorene/dibenzofuran molar ratio of not more than 0.05, and subsequently subjecting the dibenzofuran fraction thus obtained to continuous crystallization purification thereby effecting separation and recovery of dibenzofuran.

When coal tar is distilled, various coal tar fractions having different boiling point ranges are obtained. The designations of these fractions and their ranges of boiling points have not been standardized. In one system, for example, a fraction boiling in the range of 90° to 170° C. is called light oil, a fraction boiling in the range of 170° to 200° C. as carbolic oil, a fraction boiling in the range of 200° to 250° C. as naphthalene oil, a fraction boiling in the range of 230° to 280° C. as wash oil, a fraction boiling above 280° C. as anthracene oil, and the residue containing high-boiling substances and boiling above about 350° C. as pitch. The dibenzofuran contents in these fractions, though variable with the particular type of coal tar and the conditions of distillation, the typical value is shown below by way of example.

|  | Naphthalene (% by weight) | Acenaphthene (% by weight) | Dibenzofuran (% by weight) | Fluorene (% by weight) |
|---|---|---|---|---|
| Naphthalene oil | 57.5 | 1.5 | 0.7 | — |
| Wash oil | 14.9 | 15.5 | 15.7 | 5.3 |
| Anthracene oil | 7.5 | 3.5 | 6.4 | 7.0 |

The dibenzofuran-containing coal tar fraction which is used as the starting material in the method of this invention is a fraction in which dibenzofuran is contained in a concentrated form. It comprises fractions which have boiling points desirably in the range of 220° to 300° C., preferably in the range of 250° to 300° C. For example, it is a mixture of one or more fractions taken from wash oil, anthracene oil, etc. In a typical composition of this fraction, the dibenzofuran content is 5 to 30% by weight, the naphthalene content 5 to 25% by weight, the acenaphthene content 8 to 30% by weight, the fluorene content 2 to 10% by weight, and the total content of other component 25 to 75% by weight. This composition is such that the content of acenaphthene increases relative to that of dibenzofuran when the range of boiling points shifts to the lower direction and the content of fluorene increases relative to that of dibenzofuran when the range of boiling points shifts to the higher direction.

Before the dibenzofuran-containing coal tar fraction is subjected to continuous crystallization purification, it must be subjected to preliminary distillation to produce a dibenzofuran fraction which has a dibenzofuran content of not less than 30% by weight, more desirably 40 to 90% by weight, and most desirably 40 to 70% by weight, a dibenzofuran/acenaphthene molar ratio of not less than 1.3, more desirably not less than 1.5, and most desirably not less than 2.5, and a fluorene/dibenzofuran molar ratio of not more than 0.05, more desirably not more than 0.035, and most desirably not more than 0.025.

The dibenzofuran/acenaphthene molar ratio has its lower limit at 1.3. If the acenaphthene content in the dibenzofuran fraction is higher, the temperature of crystallization in an effort to heighten the yield of dibenzofuran inevitably falls to a level which is apt to result in simultaneous crystallization of acenaphthene and dibenzofuran and consequent degradation of the purity of the product. If the acenaphthene content increases to exceed the allowable limit, acenaphthene crystallizes from the beginning and makes it no longer feasible to recover dibenzofuran as a product of high purity. A possible reason for this undesirable result may be that in such a molar ratio, acenaphthene and dibenzofuran form a eutectic mixture.

The fluorene/dibenzofuran molar ratio has its upper limit at 0.05. If the molar ratio exceeds this upper limit, the fluorene content in the crystals of the product obtained in consequence of the crystallization of the dibenzofuran fraction becomes greater than that in the raw material. A possible reason for this undesirable result may be that since the molecule of dibenzofuran and that of fluorene are so similar in shape as to form a solid solution.

The dibenzofuran content has its lower limit at 30% by weight. The reason for this lower limit is that both yield and purity of the product are lowered when the content falls below the lower limit. However, an effort to heighten the dibenzofuran content beyond 95% by weight solely by the distillation does not prove to be beneficial. Preferably, therefore, the distillation is required to heighten the dibenzofuran content to a level falling in the range of 40 to 70% by weight.

In the distillation of the dibenzofuran/containing coal tar fraction, if attention is only paid to the change of the dibenzofuran content during the distillation, it is difficult to obtain a dibenzofuran fraction which satisfies both the conditions on the dibenzofuran/acenaphthene molar ratio and fluorene/dibenzofuran molar ratio. It is, therefore, imperative that this distillation should be carried out with due attention paid not merely to the condition of the dibenzofuran content but equally to that of the dibenzofuran/acenaphthene molar ratio and that of the fluorene/dibenzofuran molar ratio.

The distillation of the dibenzofuran-containing coal tar fraction may be carried out in a batchwise operation or a continuous operation or the combination of both. Besides, the distillation mat be performed either under a vacuum or under atmospheric pressure. For the purpose of this invention, the distillation under atmospheric pressure is sufficient. Suitable methods of distillation available for this invention are as follows.

One suitable method comprises subjecting the aforementioned coal tar fraction to batchwise distillation to obtain a dibenzofuran fraction having the afore-mentioned composition. Another suitable method comprises subjecting the aforementioned coal tar fraction to distillation in a first distillation column to remove low-boiling components and subjecting the resultant bottom oil in the first distillation column to batchwise or continuous distillation in a second distillation column to remove high-boiling components and to obtain a dibenzofuran fraction of the aforementioned composition. Yet another suitable method comprises subjecting the aforementioned coal tar fraction to distillation in a first distillation column to remove low-boiling components, subjecting the resultant bottom oil of the first distillation column to distillation in a second distillation column to remove high-boiling components, and then subjecting the resultant top stream from the second distillation column to batchwise or continuous distillation in a third distillation column to obtain a dibenzofuran fraction of the aforementioned composition.

By any of the methods of distillation described above, the dibenzofuran fraction specified above can be obtained when the conditions of distillation such as the number of stages and the reflux ratio are properly selected. In any event, the distillation is desired to be carried out under the conditions wherein the total number of stages is at least 30 and the reflux ratio is at least 5.

Purified dibenzofuran is separated and recovered by subjecting the dibenzofuran fraction obtained as described above to continuous crystallization purification. High purity dibenzofuran cannot be obtained when the dibenzofuran fraction is treated by such a batchwise method of crystallization and centrifugation as generally practised. It can be obtained in high purity only when the dibenzofuran fraction is subjected to continuous crystallization purification.

Various processes are available for continuous crystallization purification. Any of the process designed for continuous counter-current crystallization purification can be used for the continuous crystallization purification of this invention. Typical process of such processes are continuous crystallization purification disclosed by Japanese Patent Publication No. 18,521/1980, U.S. Pat. No. 3,645,699, U.S. Pat. No. 2,854,494, Japanese Patent Publication No. 40,621/1972, Japanese Patent Publication No. 17,710/1973, U.S. Pat. No. 3,796,060, etc. Preferably, the device used for this continuous crystallization purification possesses a cooling zone in one side and a heating zone for melting purified crystals in the other side, so that the raw material introduced into this device is cooled in the cooling zone to form crystals, the crystals thus formed are transferred to the heating zone, while in transit, refined through counter current contact with a melt refluxed toward the cooling zone from the heating zone, and the refined crystals are melted in the heating zone and drawn out of the device. Among the devices of such preferred construction most suitable one is the refining device of the shape of a vertical column disclosed by Japanese Patent Publication No. 18,521/1980. This device is provided at a suitable position of the vertical column with a feed inlet for the raw material, at the upper portion thereof with cooling means, at the lower portion thereof with heating means, at the upper portion thereof with an outlet for the mother liquor and at the bottom thereof with an outlet for the product. Across the vertical extent of the column in the downward direction, a cooling and crystallizing section for cooling the raw material and crystallizing the product component, a crystal refining section for keeping the formed crystals in counter current contact with a liquid reflux, and a melting section for melting the refined crystals are laid serially in a mutually connected state. This device is further provided with a stirrer which generates substantially no force of transferring crystals in the vertical direction, confines its stirring motion within one plane and, enables the crystals to be retained at least in a fluidized state within the liquor.

BEST MODE OF CARRYING OUT THE INVENTION

The coal tar fraction which is used in the method of the present invention is a fraction which is obtained by the distillation of coal tar and which boils at temperatures in the range of 220° to 300° C. preferably 250° to 300° C.

One preferred method for the distillation of the coal tar fraction will be described below with reference to FIG. 1. The coal tar fraction is fed via a line 1 to a batchwise distillation column 2. The batchwise distillation column 2 is an ordinary distillation column provided with at least 30, preferably at least 50, stages and adapted to be operated at a reflux ratio of at least 5, preferably at least 10. If the number of stages is smaller and the reflux ratio is lower than indicated above, effective separation of dibenzofuran from other components in the coal tar fraction, especially acenaphthene, having about the same boiling points with dibenzofuran cannot be obtained, consequently the desired acquisition of a dibenzofuran fraction having the aforementioned composition becomes impracticable.

Under such conditions as mentioned above, the coal tar fraction is thermally distilled and the low-boiling fraction consequently separated therefrom is led out of the top of the column and removed via a line 3. The amount of the low-boiling fraction so separated is variable with the particular composition of the coal tar fraction used as the raw material. In any event, at least 60%, preferably at least 70%, by weight of the acenaphthene contained in the coal tar fraction is desired to be removed as the low-boiling fraction. Consequently, the naphthalene oil composed mainly of naphthalene, β-methyl naphthalene, biphenyl, acenaphthene, etc. is separated. The fraction which is subsequently distilled out of the top of the column is drawn out via a line 4. Thus, a dibenzofuran fraction having a dibenzofuran content of at least 50% by weight, a dibenzofuran-/acenaphthene molar ratio of at least 1.5, and a fluorene/dibenzofuran molar ratio of not more than 0.05 is obtained. After this dibenzofuran fraction has been obtained, the distillation is discontinued and the bottom oil of the column is withdrawn via a line 5. The aforementioned dibenzofuran fraction is fed via a line 4 to a continuous crystallization purification unit 6.

Figure 3:
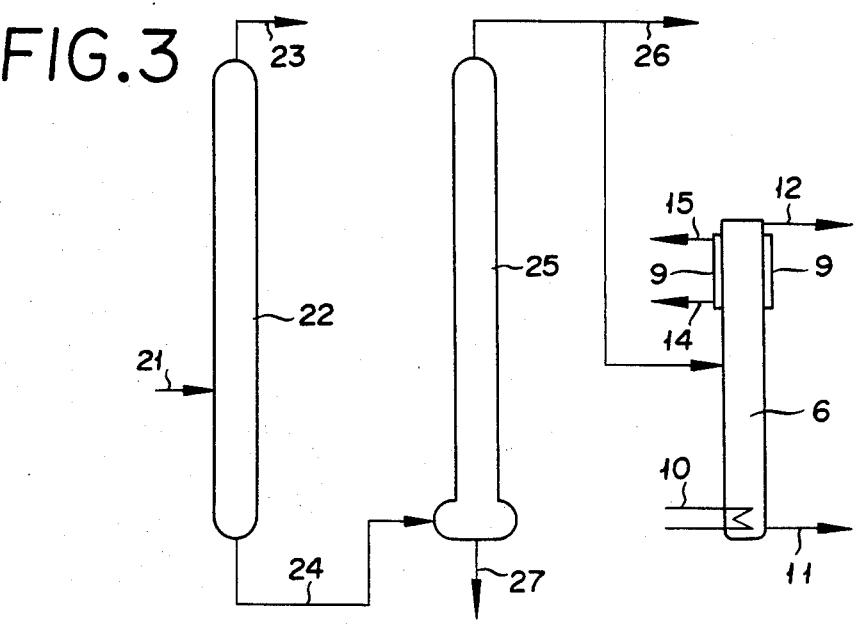
FIG. 3 is a flow sheet illustrating another preferred embodiment of the present invention.

Another preferred method for the distillation of the coal tar fraction is illustrated in FIG. 3. The coal tar component is fed via a line 21 to a first distillation column 22. The first distillation column is an ordinary continuous distillation column, which is provided with at least 30, preferably at least 50, stages and adapted to be operated at a reflux of at least 5, preferably at least 10. If the number of stages is smaller and the reflux ratio is lower than indicated above, effective separation of dibenzofuran from other components in the coal tar fraction, especially acenaphthene, having about the same boiling point with dibenzofuran can not be obtained consequently the desired acquisition of the dibenzofuran fraction aimed at becomes difficult.

Under the conditions described above, the coal tar fraction is distilled and the low-boiling fraction consequently separated therefrom is led out of the top of the column and removed via a line 23. The amount of the low-boiling fraction to be separated from the coal tar fraction is variable with the particular composition of the coal tar fraction used as the raw material. In any event, at least 60%, preferably at least 70%, by weight of the acenaphthene contained in the coal tar fraction is desired to be removed as the low-boiling fraction. Consequently, the naphthalene oil composed mainly of naphthalene, β-methyl naphthalene, biphenyl, acenaphthene, etc. is separated as the low-boiling fraction. The bottom oil in the column is fed via a line 24 to a second distillation column 25. This second distillation column may be in a batchwise or continuous operation. In the case of a batchwise distillation, the bottom oil withdrawn from the first distillation column 22 is fed via the line 24 to the bottom of the second distillation column 25 and then subjected to batchwise distillation with the temperature of the column bottom kept at 310° to 330+ C. The second distillation column is an ordinary batchwise distillation column, which is provided with at least 30 stages and adapted to operate at a reflux ratio of at least 5, preferably at least 10. In the second distillation column 25, the acenaphthene oil consisting mainly of acenaphthene is separated as the first fraction when separation of acenaphthene was not efficiently performed in the first distillation column. This first fraction is removed via a line 26. Thereafter, a dibenzofuran fraction having a dibenzofuran content of at least 50% by weight, a dibenzofuran/acenaphthene molar ratio of at least 1.5, and a fluorene/dibenzofuran molar ratio of not more than 0.05 obtained. Separately, a fluorene oil consisting mainly of fluorene is separated as the higher fraction and removed via a line 27. The aforementioned dibenzofuran fraction is fed via the line 4 to the continuous crystallization unit 6.

In case the second distillation coulmn 25 is designed for continuous distillation, the fraction transferred via the line 24 is fed into the middle stage of the distillation column 25 to be subjected to rectification. In consequence of this rectification, the acenaphthene oil is separated out of the top of the column and the fluorene oil is separated out of the bottom of the column. Consequently, a dibenzofuran fraction having the afore-mentioned composition is obtained through the middle stage of the column and fed to the continuous crystallization unit 6.

When sharp separation of acenaphthene was efficiently obtained in the first distillation column, the withdrawal of the dibenzofuran fraction through the middle stage of the column may be omitted and this fraction may be obtained through the top of the column.

Figure 4:
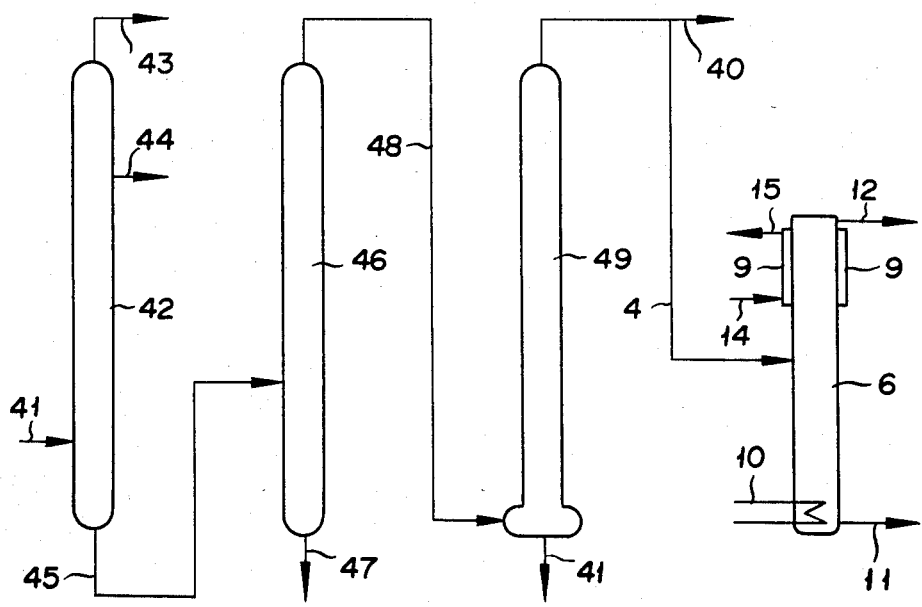
FIG. 4 is a flow sheet illustrating yet another preferred embodiment of the present invention.

Yet another preferred method for the distillation of the coal tar fraction is illustrated in FIG. 4. Here, the coal tar fraction is fed via a line 41 to a first distillation column 42, there to be subjected to continuous distillation with the temperature of the bottom of the column kept at 300° to 330° C. By this distillation, a low-boiling fraction having boiling points of 220° to 225° C. is separated through the top of the column and removed via a line 43. Consequently, the naphthalene oil consisting mainly of naphthalene, β-methyl naphthalene, α-methyl naphthalene, indene, etc. is separated.

The intermediate oil is removed via a line 44. Consequently, the acenaphthene oil consisting (mainly) of acenaphthene, biphenyl and dimethyl naphthalene is removed. The removal of the intermediate oil is aimed at heightening as much as possible the concentration of naphthalene in the naphthalene oil removed via the line 43. If the elevation of the naphthalene concentration is not required, the removal of the fraction via the line 43 alone is continued and that of the fraction via the line 44 may be omitted. The bottom residue of the column is fed via a line 45 to a second distillation column 46, there to be subjected to continuous distillation with the temperature of the bottom of the column kept at 330° to 350° C. By this continuous distillation, a high-boiling fraction boiling at or above 300° C. is separated through the bottom of the column and removed via a line 47. Consequently, fluorene, the higher fraction of fluorene, pitch, etc. are removed.

The fraction obtained in the second distillation column is fed via a line 48 to a third distillation column 49. The third distillation column may be in a batchwise or continuous operation. In the case of a batchwise distillation, the top fraction obtained in the second distillation column 46 by the removal of pitch and other fraction is fed via a line 48 to the third distillation column 49, there to be subjected to batchwise distillation with the temperature of the bottom of the column kept at 290° to 320° C. In the third distillation column 49, the acenaphthene oil consisting mainly of acenaphthene is separated as the initial fraction and removed via a line 40. In consequence of the removal of this initial fraction, a dibenzofuran fraction having a dibenzofuran content of not less than 70% by weight, a dibenzofuran/acenaphthene molar ratio of not less than 10, and a fluorene/dibenzofuran molar ratio of not more than 0.025 is obtained. Separately, the fluorene oil consisting mainly of fluorene is separated as the higher fraction and removed via a line 41. The aforementioned dibenzofuran fraction is fed via the line 4 to the continuous crystallization unit 6. The dibenzofuran fraction having the aforementioned composition can be obtained when the conditions of each of the first through third distillation columns are selected so that the number of stages is at least 30, preferably 50, and the reflux ratio is at least 5, preferably 10. In the case of the third distillation column 49 is designed for continuous distillation, the fraction withdrawn from the line 48 is fed to the middle stage of the distillation column 49 and subjected to rectification. In consequence of the rectification, the acenaphthene oil is separated through the top of the column and the fluorene oil through the bottom of the column and the dibenzofuran fraction of the aforementioned composition is obtained through the middle stage of the column. This dibenzofuran fraction is fed to the continuous crystallization unit 6.

Figure 2:
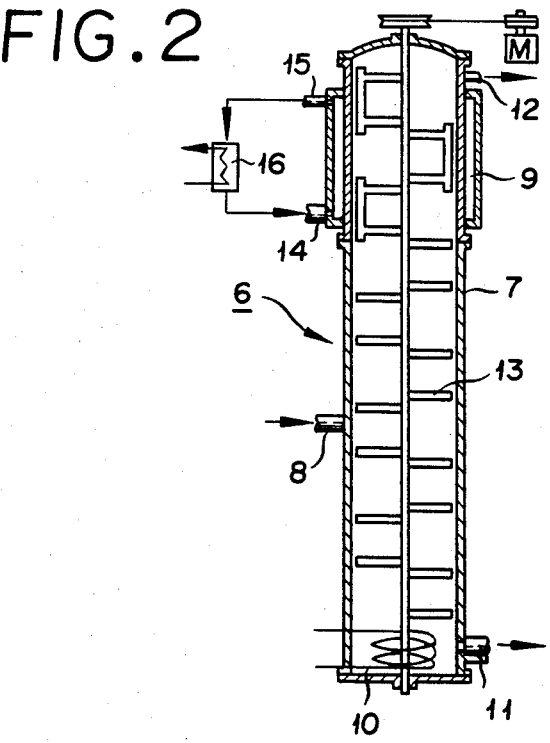
FIG. 2 is a schematic cross section illustrating a typical device for continuous crystallization purification to be used in working the process of the present invention.

The dibenzofuran fraction obtained as described above is subjected to continuous crystallization purification. Preferred continuous crystallization unit is illustrated in FIG. 2 at 6, and has a vertically-disposed crystallizing column 7 provided with a feed inlet 8 intermediate its top and bottom, a cooling jacket 9, a heating means 10 and a product outlet 11 in the lower portion, a mother liquor outlet 12 in the uppermost portion, and a stirrer 13, stirring only in horizontal plane and retain crystals in a fluidized state, is provided.

The vertical continuous crystallization unit is filled with the fraction of the aforementioned composition in a liquid state, and the stirrer is set rotating. From a cooler 16, cooling water is fed via a water inlet 14 to the jacket 9 to cool the liquid inside the column. The water departing from an outlet 15 is returned to the cooler for cyclic use. As the temperature of the cooling water is lowered, the temperature of the liquid inside the column is gradually lowered. When the temperature of this liquid reaches near the freezing point of the liquid, crystals of dibenzofuran begin to form in the liquid. The crystals thus formed sediment because they have a higher density than the surrounding liquid. When the sedimentation of crystals does not proceed smoothly, enhancement of the density difference between crystal and liquid as by the addition of a solvent may effectively aid in expediting the sedimentation. The temperature of the jacketed cooling zone of the column is further lowered and then retained at a fixed level. The amount of crystals formed in the liquid increases as the temperature of the cooling zone is lowered. If the temperature is lowered excessively, however, there is the possibility that the efficiency of the sedimentation of crystals will be degraded and the whole portion of the crystal will be held within the cooling zone of the column. The temperature of the cooling zone has its own proper lower limit which depends on the composition of the raw material. When the concentrated dibenzofuran fraction is used, the lower limit of the temperature is determined by the proportion of the total amount of high-melting substances such as acenaphthene, dibenzofuran and fluorene to the amount of the raw material It generally falls in the range of 15° to 75° C. It is particularly advantageous for the temperature of the mother liquor withdrawn via the line issuing from the top of the column to be maintained in the range of 20° to 70° C., preferably 35° to 45° C.

As crystals are gradually accumulated in the bottom zone of the column, use of the heater 10 is started. This heater may be of a suitable type using steam, a high-temperature thermal medium, or electric power as its heat source. When the heating is started, the crystals accumulated in the bottom zone are melted and the molten mass of crystals ascend in a liquid state through the column. During this ascent, the molten mass of crystals comes into counter current contact with those crystals which are sedimenting through liquid. Consequently, the mother liquor adhering to the boundaries of crystals is washed off. Refinement of the dibenzofuran gradually proceeds owing to the counter current contact between the sedimenting crystals and the ascending mass of molten crystals. The temperature of the liquid in the bottom zone of the column rises in proportion as the purity of the liquid increases. When this temperature has approached to the melting point of the product, the liquid in the bottom zone is withdrawn via the line 12. Generally it is desirable that this withdrawal of the liquid from the bottom zone is effected while the temperature of the heating zone of the column is maintained in the range of 75° to 83° C. In the meantime, introduction of the raw material is started and the continuous operation is commenced. The raw material is generally introduced in a liquid state. Optionally, it may be precooled in an external cooler and introduced in the form of slurry. The mother liquor which issued from the top of the column is drawn out of the mother liquor outlet 12 and then returned to the distillation column or utilized as a by-product oil elsewhere. The bottom liquid of the column is dibenzofuran of high purity.

Wherever "%" and "parts" are mentioned in the following working examples, they are meant "%" and "parts" by weight unless otherwise specified.

EXAMPLE 1

Figure 1:
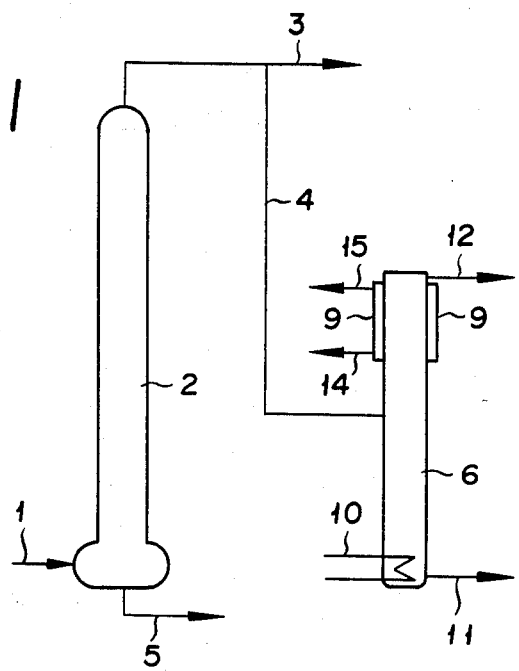
FIG. 1 is a flow sheet illustrating one preferred embodiment of this invention.

In a device constructed as illustrated in FIG. 1, 100 parts of a wash oil fraction (consisting of 17.0% of naphthalene, 7.3% of β-methyl naphthalene, 5.0% of biphenyl, 10.9% of acenaphthene, 14.9% of dibenzofuran, 12.5% of fluorene, and 32.4% of other components) obtained in the distillation of coal tar fractions having a boiling points range of 220° to 300° C. was fed through the line 1 into the batchwise distillation column (32 stages) 2 and subjected to batchwise distillation, with the temperature of the bottom of the column kept at 310° C. and the reflux ratio at 10. In this batchwise distillation, 50.6 parts of a light fraction consisting mainly of naphthalene, β-methyl naphthalene, biphenyl and acenaphthene was removed from the top of the column. Then, the fraction remaining in the still was made up to 100 parts by addition thereto of 33.0 parts of a residual oil from crystallization purification (having a dibenzofuran concentration of about 50%) and 17.6 parts of the aforementioned wash oil. At this point, the contents of the distillation column were composed of 7.8% of naphthalene, 3.6% of β-methyl naphthalene, 2.6% of biphenyl, 13.9% of acenaphthene, 36.0% of dibenzofuran, 13.9% of fluorene and 22.2% of other components. The batchwise distillation was further continued under the same conditions as described above. Consequently, 27.7 parts of an initial fraction was removed and 19.9 parts of a dibenzofuran fraction (consisting of 0.1% of naphthalene, 0.1% of β-methyl naphthalene, 0.2% of biphenyl, 14.0% of acenaphthene, 63% of dibenzofuran, 1.5% of fluorene, and 21.1% of other components) was obtained.

Via the line 4, 100 parts of this dibenzofuran fraction (having a dibenzofuran content of 63.0%, a dibenzofuran/acenaphthene molar ratio of 4.2, and a fluorene/dibenzofuran molar ratio of 0.024) was fed to the continuous crystallization unit 6, and cooled the top and heated the bottom of the column. Continuous operation of the unit was started after the temperature of the bottom of the column reached 82° C. The temperature of the cooling zone was retained at 35° C. The continuous operation was carried out for 70 hours, with the mother liquor continuously withdrawn via the line 12 and the product via the line 11. During this continuous operation, the amounts of the mother liquor and the product withdrawn from the column were 54.4 parts/hr and 43.6 parts/hr respectively. The average composition of the product was 96.4% of dibenzofuran, 0.85% of acenaphthene, 1.80% of fluorene, and the balance of other components. The average composition of the mother liquid was 38.5% of dibenzofuran, 25.1% of acenaphthene, 1.3% of fluorene, and the balance of other components.

EXAMPLE 2

In the same device as used in Example 1, 100 parts of a wash oil fraction (consisting of 13.8% of naphthalene, 4.0% of β-methyl napththalene 6.3% of biphenyl, 16.0% of acenaphthene, 15.6% of dibenzofuran, 5% of fluorene and the balance of other components) obtained in the distillation of coal tar fraction having a boiling point range of 220° to 300° C. was fed via the line 1 into the batchwise distillation column (50 stages) 5 and subjected to batchwise distillation with the temperature of the bottom of the column kept at 320° C. and the reflux ratio at 10. In this batchwise distillation, 56.0 parts of an initial fraction (consisting of 24.7% of naphthalene, 7.1% of β-methyl naphthalene, 11.2% of biphenyl, 21.5% of acenaphthene, 3.7% of dibenzofuran and the balance of other components) was withdrawn and 15.8 parts of a dibenzofuran fraction (consisting of 24.5% of acenaphthene, 61.5% of dibenzofuran, 1.2% of fluorene and the balance of other components) was obtained. At this point, 28.2 parts of the residue was obtained. This residue was composed of 0.2% acenaphthene, 13.7% of dibenzofuran, 17.0% of fluorene and the balance of other components.

Via the line 4, 15.8 parts/hr of the dibenzofuran fraction[(having a dibenzofuran content of 63.0%, a dibenzofuran/acenaphthene molar ratio of 2.5, and a fluorene/dibenzofuran molar ratio of 0.019)] was fed to the continuous crystallization unit 6, and cooled the top and heated the bottom of the column. Continuous operaiton of the unit was started after the temperature of the bottom of the column reached 81.5° to 82° C. The temperature of the cooling zone was retained at 42° to 43° C. The continuous operation was carried out for 70 hours, with the mother liquor continuously withdrawn via the line 12 and the product via the line 11. During this continuous operation, the amounts of the mother liquor and the product withdrawn from the column were 11.0 parts/hr and 4.8 parts/hr respectively. The average composition of the product was 96.4% of dibenzofuran, 0.95% of acenaphthene, 1.55% of fluorene, and the balance of other components. The average composition of the mother liquor was 46.3% of dibenzofuran, 34.7% of acenaphthene, 1.03% of fluorene and the balance of other components.

EXAMPLE 3

In the same device as used in Example 1, a wash oil fraction obtained in the distillation of coal tar fraction having a boiling point range of 220° to 300° C. was placed in a 30-stage batchwise distillation column with the reflux ratio fixed at 5 to 6. Consequently, there was obtained a dibenzofuran fraction consisting of 19.5% of acenaphthene, 56.0% of dibenzofuran, 1.2% of fluorene and 23.3% of other components.

This dibenzofuran fraction (having a dibenzofuran-/acenaphthene molar ratio of 2.63 and a fluorene/dibenzofuran molar ratio of 0.022) as a raw material was subjected to continous crystallization purification. Continuous operation of the unit was started after the temperature of the bottom of the column reached 83° C. The temperature of the cooling zone was retained at 25° C. The continuous operaiton was carried out for 40 hours. During this continuous operation, the amount of the raw material fed to the unit and the amount of the product withdrawn therefrom averaged 512 parts/hr and 167 parts/hr respectively. The average composition of the product was 95.2% of dibenzofuran, 1.5% of acenaphthene and 1.8% of fluorene. The average composition of the mother liquor discharged out of the top of the column was 36.5% of dibenzofuran, 28.1% of acenaphthene, 1.0% of fluorene. The dibenzofuran- /acenaphthene molar ratio, therefore, was 1.19. The yield of the product against the raw material was 32.6% and the proportion of dibenzofuran in the product to the dibenzofuran contained in the raw material was 55.5%.

Separately, 60 parts of the raw material for the crystallization and 40 parts of the mother liquor both of Example 3 were mixed to obtain a second raw material consisting of 44.3% of dibenzofuran, 25.0% of acenaphthene, 1.1% of fluorene and 29.6% of other components (therefore, having a dibenzofuran/acenaphtheen molar ratio of 1.62 and a fluorene/dibenzofuran molar ratio of 0.025). The second raw material was subjected to continuous crystallization under the same conditions as those described above, except that the temperature of the cooling zone was kept at 20° C.

During this continuous crystallization, the amount of the raw material fed to the unit and the amount of the product withdrawn therefrom averaged 294 parts/hr and 62 parts/hr respectively. The average composition of the product was 96.3% of dibenzofuran, 1.2% of acenaphthene and 1.3% of fluorene. The average composition of the mother liquor discharged from the top of the column was 30.7% of dibenzofuran, 27.8% of acenaphthene and 1.0% of fluorene and, consequently, the dibenzofuran/acenaphtene molar ratio was 1.01. The yield of the product against the raw material was 21.1% and the proportion of dibenzofuran in the product to the dibenzofuran contained in the raw material was 45.9%.

For the purpose of comparison, 200 parts of the same dibenzofuran fraction (having a dibenzofuran content of 56.0%) as used in Exmaple 3 was placed in a flask provided with a stirrer. The flask containing the fraction was immersed in a constant temperature bath kept at 70° C. until perfect melt of the fraction. Then, the contents of the flask were stirred (at 130 rpm) and the temperature thereof was gradually lowered to 35° C. causing crystallization. The slurry consequently obtained was placed in a centrifugal separator provided with a basket and centrifuged at 3,200 rpm for 10 minutes. Consequently 36 parts (yield 18%) of crystal was obtained the composition of which was 87.2% of dibenzofuran, 6.8% of acenaphthene and 2.2% of fluorene.

EXAMPLE 4

In a device constructed as illiustrated in FIG. 3, a wash oil fraction (consisting of 13.8% of napththalene, 16.0% of acenaphthene, 15.6% of dibenzofuran, 5.2% of fluorene and the balance of other components) obtained in the distillation of coal tar fraction having a boiling point range of 220° to 300° C. was fed at at a rate of 100 parts/hr via the line 21 to the first distillation column (50 stages) 22 and subjected to continuous distillation with the temperature of the bottom of the column kept at 300.1° C. and the reflux ratio at 10. By this continuous distillation, naphthanlene oil (consisting of 26.6% of naphthalene, 19.4% of acenaphthene, 1.0% of dibenzofuran, 0% of fluorene and the balance of other components) was separated as the top fraction at a rate of 52 parts/hr via the line 23. The bottom oil (consisting of 12.2% of acenaphthene, 31.6% of dibenzofuran, 10.9% of fluorene and the balance of other components) remainting in the column was fed in an amount of 48 parts to the bottom of the second distillation column (30 stages) 25. In the second distillation column 25, batchwise distillation was effected with the temperature of the bottom of the column kept at 325° C. and the reflux ratio at 5. By this batchwise distillation, 2.3 parts of an initial fraction (consisting of 41.2% of acenaphthene, 43.4% of dibenzofuran, 0.22% of fluorene and the balance of other components) was separated and 13.8 parts of a dibenzofuran fraction (consisting of 29.5% of acenaphthene, 55.9% of dibenzofuran, 1.7% of fluorene and the balance of other components) was obtained. At this point, 31.9 parts of the bottom oil remained. The composition of the bottom oil was 2.7% of acenaphthene, 20.2% of dibenzofuran, 15.7% of fluorene and the balance of other components.

Via the line 7, this dibenzofuran fraction (having a dibenzofuran content of 55.9%, a dibenzofuran/acenaphthene molar ratio of 1.89 and a fluorene/dibenzofuran molar ratio of 0.031) was fed at a rate of 13.8 parts/hr to the continuous crystallization unit 6, and cooled the top and heated the bottom of the column. The temperature of the cooling zone was maintained at 43° to 44° C. The continuous operation was carried out for 70 hours, with the mother liquid continuously removed via the line 15 and the product via the line 11. During the continuous operation, the amount of the mother liquor and that of the product withdrawn from the column averaged 11.4 parts/hr and 2.4 parts/hr respectively. The average composition of the product was 96.1% of dibenzofuran, 1.02% of acenaphthene, 2.1% of fluorene and the balance of other components. The average composition of the mother liquor was 47.4% of dibenzofuran, 35.5% of acenaphthene, 1.7% of fluorene and the balance of other components.

EXAMPLE 5

After the procedure of Example 4, a wash oil fraction having the same composition as used in Example 3 was subjected in the first distillation column to continuous distillation under the same conditions as those of Example 3. The bottom residue of the column was fed at a rate of 48 parts/hr to the middle stage of the second distillation column (50 stages) and subjected to continuous distillation with the temperature of the bottom of the column kept at 342.3° C. and the reflux ratio at 10. By this continuous distillation, a dibenzofuran fraction (consisting of 29.0% of acenaphthene, 57.5% of dibenzofuran, 0.85% of fluorene and the balance of other components) was obtained at a rate of 20 parts/hr through the top of the column. A bottom oil (consisting of 13.0% of dibenzofuran, 18.1% of fluorene, and the balance of other portions) was obtained at a rate of 28 parts/hr.

This dibenzofuran fraction (having a dibenzofuran content of 57.5%, a dibenzofuran/acenaphthene molar ratio of 1.82 and a fluorene/dibenzofuran molar ratio of 0.015) was fed at a rate of 20 parts/hr to the continous crystallization unit, and cooled the top and heated the bottom of the column. Continuous operation of this unit was started after the temperature of the bottom of the column reached 82° to 82.3° C. The temperature of the cooling zone was kept at 43° to 44° C. The continuous operation was carried out for 70 hours, with the mother liquor and the product continuously withdrawn separately from the column. During this continuous operation, the amount of the mother liquor and that of the product withdrawn from the column averaged 16.0 parts/hr and 4.0 parts/hr respectively. The average composition of the product was 96.6% of dibenzofuran, 0.92% of acenaphthene, 1.2% of fluorene and the balance of other components. The average composition of the mother liquid was 47.9% of dibenzofuran, 35.9% of acenaphthene, 0.76% of fluorene and the balance of other components.

EXAMPLE 6

In a device constructed as illustrated in FIG. 4, a wash oil fraction (consisting of 13.8% of naphthalene, 6.1% of methyl naphthalenes, 16.0% of acenaphthene, 15.6% of dibenzofuran, 5.2% of fluorene and the balance of other components) was fed at a rate of 100 parts/hr via the line 41 to the first distillation column (60 stages) 42 and subjected to continuous distillation with the temperature of the bottom of the column kept at 320° C. and the reflux ratio at 20. By this continuous distillation, a naphthalene oil (consisting of 66.4% of naphthalene, 14.2% of methyl naphthalenes, 1.0% of acenaphthene, 0.1% of dibenzofuran and the balance of other components) was separated as the top fraction in a rate of 18 parts/hr via the line 43, an acenaphthene oil (consisting of 31.1% of acenaphthene, 19.7% of diemthyl naphthalenes, 14.6% of biphenyl, 13.2% of methyl biphenyl and the balance of other components) was separated as the upper middle (12th stage) fraction in a rate of 36 parts/hr via the line 44, and the bottom oil of the column was fed at a rate of 46 parts/hr via the line 45 to the second distillation column (60 stages) 46. In the second distillation column 46, the charged bottom oil was subjected to continuous distillation with the temperature of the bottom of the column kept at 340° C. and the reflux ratio at 10. By this continuous distillation, a high-boiling oil (consisting of 0.6% of dibenzofuran, 7.4% of fluorene, 5.3% of methyl fluorene, 2.5% of anthracene and phenanthrene and the balance of other components) was removed as the bottom fraction at a rate of 20.24 parts/hr via the line 41 and a top fraction (consisting of 17.8% of acenaphthene, 55.8% of dibenzofuran, 14.5% of fluorene and the balance of other components) was obtained in a rate of 25.76 parts/hr via the line 48. The bottom fraction removed as described above was combined with the acenaphthene oil removed via the line 44 from the first distillation column, and the resultant mixture as a by-product of distillation was suitable for the preparation of a wash oil.

In the third distillation column (60 stages) 49, 25.76 parts of the top fraction from the second distillation column was subjected to batchwise distillation with the temperature of the bottom of the column kept at 300° C. and the reflux ratio at 40. By this batchwise distillation 6.41 parts of an acenaphene oil (consisting of 62.7% of acenaphthene, 16.6% of dibenzofuran and the balance of other components) was removed as the initial fraction via the line 40. Then a dibenzofuran fraction (consisting of 3.9% of acenaphthene, 88.4% of dibenzofuran, 0.15% of fluorene and the balance of other components) was obtained as the main fraction and fed via the line 4 to the continuous crystallization unit 6. After the withdrawal of the main fraction, 4.70 parts of a fluorene oil (consisting of 8.0% of dibenzofuran, 78.9% of fluorene and the balance of other components) was removed as the fraction via the line 41.

Then, the dibenzofuran fraction (having a dibenzofuran content of 88.4% a dibenzofuran/acenaphthene molar ratio of 20.8 and a fluorene/dibenzofuran molar ratio of 0.0002) was fed at a rate of 14.65 parts/hr to the continuous crystallization unit 6, and cooled the top and heated in the bottom of the column with the procedure described above. Continuous operation of the unit was started after the temperature of the bottom of the column reached 82° C. The temperature of the cooling zone was kept at 37° C. The continuous operation was carried out for 70 hours. During the continuous operation, the amount of the raw material fed and the amount of the product withdrawn therefrom respectively averaged 14.65 parts/hr and 12.45 parts/hr. The average composition of the product was 97.0% of dibenzofuran, 1.0% of acenaphthene, 0.2% of fluorene and the balance of other components. From the top of the column, the mother liquor was discharged at a rate of 2.20 parts/hr. The average composition of this mother liquor was 39.8% of dibenzofuran, 20.3% of acenaphthene, 0.1% of fluorene and the balance of other components.

We claim:

1. A process for producing dibenzofuran of at least 95% purity, characterized by the steps of distilling a dibenzofuran-containing coal tar fraction predominantly composed of components boiling at temperatures in the range of 220° to 300° and thereby producing a dibenzofuran fraction having a dibenzofuran content of 40% to 90% by weight, a dibenzofuran/acenaphthene molar ratio of not less than 1.3, and a fluorene/dibenzofuran molar ratio of not more than 0.05, and subsequently subjecting said dibenzofuran fraction to continuous crystallization purification thereby separating and recovering dibenzofuran, wherein the continuous crystallization is effected by continuously feeding said dibenzofuran fraction into a continuous crystallization column provided with a cooling zone at the top thereof for crystallizing dibenzofuran from the dibenzofuran fraction fed thereto, a heating zone at the bottom thereof for melting of the formed crystals as they sink to the bottom, and a refining zone in between said cooling and heating zones for enabling the formed crystals as they sink from said cooling zone to said heating zone to come into counter current contact with and to pass through and be washed by a mass of molten crystals along the path between said cooling and heating zones, wherein the temperature of the cooling zone is kept in the range of 20° to 70° C., and the temperature of the heating zone is kept in the range of 75° to 83° C., and wherein said dibenzofuran fraction is fed into said column between said cooling and heating zones, mother liquor is continuously withdrawn from said cooling zone, and molten crystals are continuously withdrawn from said heating zone at rates which maintain a mass of molten crystals in said column to wash the formed crystals as they sink to the bottom of said column.

2. A process of claim 1, wherein the mother liquor from the continuous crystallization is not recycled.

3. A process according to claim 2, wherein the coal tar fraction is at least one fraction selected from the group consisting of wash oil and anthracene oil.

4. A process of claim 2, wherein the distillation of the dibenzofuran-containing coal tar fracton is effected batchwise and low-boiling components are removed therefrom as an initial fraction.

5. A process according to claim 2, wherein the distillation of the dibenzofuran-containing coal tar fraction is effected by removing low-boiling components therefrom by distilling said coal tar fraction in a distillation column and them removing high-boiling components therefrom by subjecting the bottom oil of said distillation column to distillation in a final distillation column.

6. A process according to claim 2, wherein the distillation of the dibenzofuran-containing coal tar fraction is effected by removing low-boiling components therefrom by distilling said coal tar fraction in a distillation column, then removing high-boiling components therefrom by subjecting the bottom oil of said distillation column to distillation in an intermediate distillation column, and subjecting the top fraction obtained in said intermediate distillation column to distillation in a final distillation column thereby separating a dibenzofuran fraction.

7. A process of claim 4, wherein the coal tar fraction is at least one fraction selected from the group consisting of wash oil and anthracene oil.

8. A process of claim 5, wherein the dibenzofuran-containing coal tar fraction fed to the first-named distillation column is at least one fraction selected from the group consisting of wash oil and anthracene oil.

9. A process of claim 6, wherein the dibenzofuran-containing coal tar fraction fed to the first-named distillation column is at least one fraction selected from the group consisting of wash oil and anthracene oil.

10. A process for producing dibenzofuran of at least 95% purity, characterized by continually introducing a dibenzofuran coal tar-derived fraction having a dibenzofuran/acenaphthene molar ration of not less than 1.3 and a fluorene/dibenzofuran molar ratio of not more than 0.05 into a continuous crystallizing unit comprising a cooling and crystallizing zone and heating and melting zones wherein the temperature in the cooling zone is kept in the range of 20° to 70° C. and the temperature in the heating zone is kept in the range of 75° to 83° C., wherein the continuous crystalization is effected by cooling the dibenzofuran fraction in said cooling zone to a crystallizing temperature in the said range of 20° to 70° C., thereby causing dibenzofuran crystals to form, allowing the formed crystals to freely sediment, melting the sedimenting crystals in said heating zone and accumulating a mass of molten crystals which function to wash the sedimenting crystals in their transit from the cooling zone to the heating zone, withdrawing molten crystals from the heating zone at a temperature in the range of 75° to 83° C., and, at the same time, withdrawing consequently separated mother liquor from the cooling zone at a temperature in the range of 20° to 70° C. and at rates which cause said mass of molten crystals to be formed and maintained.

11. A process of claim 10, whereing the dibenzofuran-containing coal tar fraction which is subjected to said continuous crystallization is obtained by the distillation of a coal tar fraction predominantly composed of components boiling in the range of 220° to 300° and is free of mother liquor recycled from said continuous crystallization.

12. A process of claim 11 wherein the dibenzofuran-containing coal tar fraction fed to the first named distillation column is at least one fraction selected from the group consisting of wash oil and anthracene oil.

* * * * *

UNITED STATES PATENT AND TRADEMARK OFFICE
CERTIFICATE OF CORRECTION

PATENT NO. : 4,608,127          Page 1 of 2

DATED : August 26, 1986

INVENTOR(S) : Kiyoshi Sakuma, Tadao Tomioka, Sunao Tabuchi, Kihachiro Ohta and Masakazu Takeuchi It is certified that error appears in the above-identified patent and that said Letters Patent is hereby corrected as shown below:

Title Page, the item before [57] ABSTRACT, which is "Attorney, Agent, or Firm"; delete "John J. Byrne; Bradford E. Kile; Kevin M. O'Brien" and insert -- Gordon W. Hueschen --
Col. 1, line 48; "others" should read -- other --
Col. 3, line 61; "mat" should read -- may --
Col. 6, line 5; after "reflux" insert -- ratio --
Col. 6, line 33; "330+" should read -- 330° --
Col. 6, line 46; after "0.05" insert -- is --
Col. 7, line 5; "225°" should read -- 255° --
Col. 8, line 38; after "material" insert a period -- . --
Col. 9, line 19; "points" should read -- point --
Col. 10, line 55; "continous" should read -- continuous --
Col. 10, line 59; "operaiton" should read -- operation --
Col. 11, line 31; "Exmaple" should read -- Example --
Col. 11, line 45; "illiustrated" should read -- illustrated --
Col. 11, line 50; delete "at" (first occurrence)
Col. 11, line 62; "remainting" should read -- remaining --
Col. 12, line 51; "continous" should read -- continuous --
Col. 13, lines 17 & 18; "diemthyl" should read -- dimethyl --
Col. 13, line 61; "0.0002)" should read -- 0.002) --
Col. 14, line 9; "acenapthene," should read -- acenaphthene, --
Col. 14, line 52; "fracton" should read -- fraction --

Col. 10, line 26; "operaiton" should read -- operation --

UNITED STATES PATENT AND TRADEMARK OFFICE
CERTIFICATE OF CORRECTION

PATENT NO. : 4,608,127          Page 2 of 2

DATED : August 26, 1986

INVENTOR(S) : Kiyoshi Sakuma, Tadao Tomioka, Sunao Tabuchi, Kihachiro Ohta and Masakazu Takeuchi It is certified that error appears in the above-identified patent and that said Letters Patent is hereby corrected as shown below:

Col. 15, line 26; "crystalization" should read -- crystallization --
Col. 16, line 15; "whereing" should read -- wherein --

Signed and Sealed this

First Day of September, 1987

*Attest:*

·DONALD J. QUIGG

*Attesting Officer*  *Commissioner of Patents and Trademarks*